United States Patent
Divita et al.

(10) Patent No.: US 7,579,318 B2
(45) Date of Patent: Aug. 25, 2009

(54) CELL PENETRATING PEPTIDES FOR INTRACELLULAR DELIVERY OF MOLECULES

(75) Inventors: Gilles Divita, Mauguio (FR); Frédéric Heitz, Grabels (FR); Catherine May Morris, Mauguio (FR); Gudrun Aldrian-Herrada, Prades-le-Lez (FR)

(73) Assignees: Centre de la Recherche de la Scientifique, Paris (FR); Panomics, Inc., Fremont, CA (US)

( * ) Notice: Subject to any disclaimer, the term of this patent is extended or adjusted under 35 U.S.C. 154(b) by 74 days.

(21) Appl. No.: 11/294,421

(22) Filed: Dec. 6, 2005

(65) Prior Publication Data
US 2007/0129305 A1 Jun. 7, 2007

(51) Int. Cl.
*A61K 38/00* (2006.01)

(52) U.S. Cl. ............... 514/13; 530/326; 514/44; 424/1.45

(58) Field of Classification Search ............. None
See application file for complete search history.

(56) References Cited

OTHER PUBLICATIONS

Hammer, et al., 1992, J. Exp. Med., 176, 1007-1013.*
Esteve, et al., 2001, Biopolymers 59, 467-476.*

* cited by examiner

*Primary Examiner*—Andrew D Kosar
*Assistant Examiner*—Satyanarayana R. Gudibande
(74) *Attorney, Agent, or Firm*—Oblon, Spivak, McClelland, Maier & Neustadt, P.C.

(57) ABSTRACT

The present invention concerns cell-penetrating peptides which comprise an amino acid sequence consisting of $GLX_9WRAX_9WRX_1LX_2RSLX_9WX_3X_4X_5X_6X_7X_8$ (SEQ ID No: 1), wherein $X_1$ is A, L or G, $X_2$ is W or none, $X_3$ is R or K, $X_4$ is K, L or S, $X_5$ is L or K, $X_6$ is R or W, $X_7$ is K or S, and $X_8$ is A, V or Q, and $X_9$ is W, F or Y. These CPPs can be used as vectors for delivering nucleic acids and/or proteins and/or peptides to cells, in vitro or in vivo.

5 Claims, 9 Drawing Sheets

A

B

A

B

CADY-1 (μM)

SEQUENCE LISTING

```
<160> NUMBER OF SEQ ID NOS: 27

<210> SEQ ID NO 1
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa = W, F or Y
<220> FEATURE:
<221> NAME/KEY: MISC_FEATURE
<222> LOCATION: (6)..(6)
<223> OTHER INFORMATION: Xaa = W, F or Y
<220> FEATURE:
<221> NAME/KEY: MISC_FEATURE
<222> LOCATION: (8)..(8)
<223> OTHER INFORMATION: Xaa = A, L or G
<220> FEATURE:
<221> NAME/KEY: MISC_FEATURE
<222> LOCATION: (10)..(10)
<223> OTHER INFORMATION: Xaa is absent or Xaa = W
<220> FEATURE:
<221> NAME/KEY: MISC_FEATURE
<222> LOCATION: (14)..(14)
<223> OTHER INFORMATION: Xaa = W, F or Y
<220> FEATURE:
<221> NAME/KEY: MISC_FEATURE
<222> LOCATION: (15)..(15)
<223> OTHER INFORMATION: Xaa = R or K
<220> FEATURE:
<221> NAME/KEY: MISC_FEATURE
<222> LOCATION: (16)..(16)
<223> OTHER INFORMATION: Xaa = K, L or S
<220> FEATURE:
<221> NAME/KEY: MISC_FEATURE
<222> LOCATION: (17)..(17)
<223> OTHER INFORMATION: Xaa = L or K
<220> FEATURE:
<221> NAME/KEY: MISC_FEATURE
<222> LOCATION: (18)..(18)
<223> OTHER INFORMATION: Xaa = R or W
<220> FEATURE:
<221> NAME/KEY: MISC_FEATURE
<222> LOCATION: (19)..(19)
<223> OTHER INFORMATION: Xaa = K or S
<220> FEATURE:
<221> NAME/KEY: MISC_FEATURE
<222> LOCATION: (20)..(20)
<223> OTHER INFORMATION: Xaa = A, V or Q

<400> SEQUENCE: 1

Glu Leu Xaa Arg Ala Xaa Arg Xaa Leu Xaa Arg Ser Leu Xaa Xaa Xaa
```

```
                1               5                  10                 15
Xaa Xaa Xaa Xaa
            20

<210> SEQ ID NO 2
<211> LENGTH: 20
<212> TYPE: PRT
<213> ORGANISM: Artificial
<220> FEATURE:
<223> OTHER INFORMATION: Synthetic Peptide

<400> SEQUENCE: 2

Gly Leu Trp Arg Ala Leu Trp Arg Leu Leu Arg Ser Leu Trp Arg Leu
1               5                  10                 15

Leu Trp Lys Ala
            20

<210> SEQ ID NO 3
<211> LENGTH: 21
<212> TYPE: PRT
<213> ORGANISM: Artificial
<220> FEATURE:
<223> OTHER INFORMATION: Synthetic Peptide

<400> SEQUENCE: 3

Glu Leu Trp Arg Ala Leu Trp Arg Ala Leu Trp Arg Ser Leu Trp Lys
1               5                  10                 15

Leu Lys Arg Lys Val
            20

<210> SEQ ID NO 4
<211> LENGTH: 20
<212> TYPE: PRT
<213> ORGANISM: Artificial
<220> FEATURE:
<223> OTHER INFORMATION: Synthetic Peptide

<400> SEQUENCE: 4

Gly Leu Trp Arg Ala Leu Trp Arg Ala Leu Arg Ser Leu Trp Lys Leu
1               5                  10                 15

Lys Arg Lys Val
            20

<210> SEQ ID NO 5
<211> LENGTH: 20
<212> TYPE: PRT
<213> ORGANISM: Artificial
<220> FEATURE:
<223> OTHER INFORMATION: Synthetic Peptide

<400> SEQUENCE: 5

Gly Leu Trp Arg Ala Leu Trp Arg Gly Leu Arg Ser Leu Trp Lys Leu
1               5                  10                 15

Lys Arg Lys Val
            20

<210> SEQ ID NO 6
<211> LENGTH: 20
<212> TYPE: PRT
<213> ORGANISM: Artificial
<220> FEATURE:
<223> OTHER INFORMATION: Synthetic Peptide

<400> SEQUENCE: 6
```

Glu Leu Trp Arg Ala Leu Trp Arg Gly Leu Arg Ser Leu Trp Lys Lys
1               5                   10                  15

Lys Arg Lys Val
            20

<210> SEQ ID NO 7
<211> LENGTH: 20
<212> TYPE: PRT
<213> ORGANISM: Artificial
<220> FEATURE:
<223> OTHER INFORMATION: Synthetic Peptide

<400> SEQUENCE: 7

Gly Leu Trp Arg Ala Leu Trp Arg Leu Leu Arg Ser Leu Trp Arg Leu
1               5                   10                  15

Leu Trp Lys Ala
            20

<210> SEQ ID NO 8
<211> LENGTH: 21
<212> TYPE: PRT
<213> ORGANISM: Artificial
<220> FEATURE:
<223> OTHER INFORMATION: Synthetic Peptide

<400> SEQUENCE: 8

Gly Leu Trp Arg Ala Leu Trp Arg Ala Leu Trp Arg Ser Leu Trp Lys
1               5                   10                  15

Leu Lys Trp Lys Val
            20

<210> SEQ ID NO 9
<211> LENGTH: 21
<212> TYPE: PRT
<213> ORGANISM: Artificial
<220> FEATURE:
<223> OTHER INFORMATION: Synthetic Peptide

<400> SEQUENCE: 9

Gly Leu Trp Arg Ala Leu Trp Arg Ala Leu Trp Arg Ser Leu Trp Lys
1               5                   10                  15

Ser Lys Arg Lys Val
            20

<210> SEQ ID NO 10
<211> LENGTH: 21
<212> TYPE: PRT
<213> ORGANISM: Artificial
<220> FEATURE:
<223> OTHER INFORMATION: Synthetic Peptide

<400> SEQUENCE: 10

Gly Leu Trp Arg Ala Leu Trp Arg Ala Leu Trp Arg Ser Leu Trp Lys
1               5                   10                  15

Lys Lys Arg Lys Val
            20

<210> SEQ ID NO 11
<211> LENGTH: 20
<212> TYPE: PRT
<213> ORGANISM: Artificial
<220> FEATURE:
<223> OTHER INFORMATION: Synthetic Peptide

<400> SEQUENCE: 11

Gly Leu Trp Arg Ala Leu Trp Arg Leu Leu Arg Ser Leu Trp Arg Leu
1               5                   10                  15

Leu Trp Ser Gln
            20

<210> SEQ ID NO 12
<211> LENGTH: 27
<212> TYPE: PRT
<213> ORGANISM: Artificial
<220> FEATURE:
<223> OTHER INFORMATION: Synthetic Peptide

<400> SEQUENCE: 12

Gly Leu Trp Arg Ala Leu Trp Arg Leu Leu Arg Ser Leu Trp Arg Leu
1               5                   10                  15

Leu Trp Ser Gln Pro Lys Lys Arg Lys Val
            20                  25

<210> SEQ ID NO 13
<211> LENGTH: 22
<212> TYPE: PRT
<213> ORGANISM: Artificial
<220> FEATURE:
<223> OTHER INFORMATION: Synthetic Peptide

<400> SEQUENCE: 13

Cys Ala Gly Leu Trp Arg Ala Leu Trp Arg Leu Leu Arg Ser Leu Trp
1               5                   10                  15

Arg Leu Leu Trp Lys Ala
            20

<210> SEQ ID NO 14
<211> LENGTH: 21
<212> TYPE: DNA
<213> ORGANISM: Artificial
<220> FEATURE:
<223> OTHER INFORMATION: Synthetic DNA/RNA

<400> SEQUENCE: 14
cuuacgcuga guacuucgat t                                           21

<210> SEQ ID NO 15
<211> LENGTH: 21
<212> TYPE: DNA
<213> ORGANISM: Artificial
<220> FEATURE:
<223> OTHER INFORMATION: Synthetic DNA/RNA

<400> SEQUENCE: 15
ttgaaugcga cucaugaagc u                                           21

<210> SEQ ID NO 16
<211> LENGTH: 21
<212> TYPE: DNA
<213> ORGANISM: Artificial
<220> FEATURE:
<223> OTHER INFORMATION: Synthetic DNA/RNA

<400> SEQUENCE: 16
cguacgcgga auacuucgat t                                           21

<210> SEQ ID NO 17
<211> LENGTH: 21
<212> TYPE: DNA

```
<213> ORGANISM: Artificial
<220> FEATURE:
<223> OTHER INFORMATION: Synthetic DNA/RNA

<400> SEQUENCE: 17
ttgcaugcgc cuuaugaagc u                                              21

<210> SEQ ID NO 18
<211> LENGTH: 21
<212> TYPE: DNA
<213> ORGANISM: Artificial
<220> FEATURE:
<223> OTHER INFORMATION: Synthetic DNA/RNA

<400> SEQUENCE: 18
ggcgaagauc aacauggcat t                                              21

<210> SEQ ID NO 19
<211> LENGTH: 21
<212> TYPE: DNA
<213> ORGANISM: Artificial
<220> FEATURE:
<223> OTHER INFORMATION: Synthetic DNA/RNA

<400> SEQUENCE: 19
ugccauguug aucuucgcct t                                              21

<210> SEQ ID NO 20
<211> LENGTH: 21
<212> TYPE: DNA
<213> ORGANISM: Artificial
<220> FEATURE:
<223> OTHER INFORMATION: Synthetic DNA/RNA

<400> SEQUENCE: 20
ggugaagauc agcauggcat t                                              21

<210> SEQ ID NO 21
<211> LENGTH: 21
<212> TYPE: DNA
<213> ORGANISM: Artificial
<220> FEATURE:
<223> OTHER INFORMATION: Synthetic DNA/RNA

<400> SEQUENCE: 21
ugccaugucg aucuucacct t                                              21

<210> SEQ ID NO 22
<211> LENGTH: 28
<212> TYPE: PRT
<213> ORGANISM: Artificial
<220> FEATURE:
<223> OTHER INFORMATION: Synthetic Peptide

<400> SEQUENCE: 22

Arg Val Ser Asn Gly Ser Pro Ser Leu Glu Arg Met Asp Ala Arg Gln
1               5                   10                  15

Ala Glu His Pro Lys Pro Ser Ala Cys Arg Asn Leu
            20                  25

<210> SEQ ID NO 23
<211> LENGTH: 9
<212> TYPE: PRT
<213> ORGANISM: Artificial
<220> FEATURE:
<223> OTHER INFORMATION: Synthetic Peptide
```

```
<400> SEQUENCE: 23

Pro Ser Leu Glu Arg Met Asp Ala Arg
1               5

<210> SEQ ID NO 24
<211> LENGTH: 27
<212> TYPE: PRT
<213> ORGANISM: Artificial
<220> FEATURE:
<223> OTHER INFORMATION: Synthetic Peptide

<400> SEQUENCE: 24

Asn Arg Thr Glu Glu Asn Val Ser Asp Gly Ser Pro Asn Ala Gly Ser
1               5                   10                  15

Val Glu Gln Thr Pro Lys Lys Pro Gly Leu Arg
            20                  25

<210> SEQ ID NO 25
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (8)..(8)
<223> OTHER INFORMATION: Xaa = A, L or G
<220> FEATURE:
<221> NAME/KEY: MISC_FEATURE
<222> LOCATION: (10)..(10)
<223> OTHER INFORMATION: Xaa is absent or Xaa is W
<220> FEATURE:
<221> NAME/KEY: MISC_FEATURE
<222> LOCATION: (15)..(15)
<223> OTHER INFORMATION: Xaa = R or K
<220> FEATURE:
<221> NAME/KEY: MISC_FEATURE
<222> LOCATION: (16)..(16)
<223> OTHER INFORMATION: Xaa = K, L or S
<220> FEATURE:
<221> NAME/KEY: MISC_FEATURE
<222> LOCATION: (17)..(17)
<223> OTHER INFORMATION: Xaa = L or K
<220> FEATURE:
<221> NAME/KEY: MISC_FEATURE
<222> LOCATION: (18)..(18)
<223> OTHER INFORMATION: Xaa = R or W
<220> FEATURE:
<221> NAME/KEY: MISC_FEATURE
<222> LOCATION: (19)..(19)
<223> OTHER INFORMATION: Xaa = K or S
<220> FEATURE:
<221> NAME/KEY: MISC_FEATURE
<222> LOCATION: (20)..(20)
<223> OTHER INFORMATION: Xaa = A, V or Q

<400> SEQUENCE: 25

Gly Leu Trp Arg Ala Trp Arg Xaa Leu Xaa Arg Ser Leu Trp Xaa Xaa
1               5                   10                  15

Xaa Xaa Xaa Xaa
            20

<210> SEQ ID NO 26
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
```

```
<222> LOCATION: (8)..(8)
<223> OTHER INFORMATION: Xaa = A, L or G
<220> FEATURE:
<221> NAME/KEY: MISC_FEATURE
<222> LOCATION: (10)..(10)
<223> OTHER INFORMATION: Xaa is absent or Xaa = W
<220> FEATURE:
<221> NAME/KEY: MISC_FEATURE
<222> LOCATION: (15)..(15)
<223> OTHER INFORMATION: Xaa = R or K
<220> FEATURE:
<221> NAME/KEY: MISC_FEATURE
<222> LOCATION: (16)..(16)
<223> OTHER INFORMATION: Xaa = K or L
<220> FEATURE:
<221> NAME/KEY: MISC_FEATURE
<222> LOCATION: (17)..(17)
<223> OTHER INFORMATION: Xaa = K or L
<220> FEATURE:
<221> NAME/KEY: MISC_FEATURE
<222> LOCATION: (18)..(18)
<223> OTHER INFORMATION: Xaa = R or W
<220> FEATURE:
<221> NAME/KEY: MISC_FEATURE
<222> LOCATION: (20)..(20)
<223> OTHER INFORMATION: Xaa = A or V

<400> SEQUENCE: 26

Gly Leu Trp Arg Ala Trp Arg Xaa Leu Xaa Arg Ser Leu Trp Xaa Xaa
1               5                   10                  15

Xaa Xaa Lys Xaa
            20

<210> SEQ ID NO 27
<211> LENGTH: 7
<212> TYPE: PRT
<213> ORGANISM: Artificial
<220> FEATURE:
<223> OTHER INFORMATION: Synthetic Peptide

<400> SEQUENCE: 27

Pro Lys Lys Lys Arg Lys Val
1               5
```

CELL PENETRATING PEPTIDES FOR INTRACELLULAR DELIVERY OF MOLECULES

Figure 1:
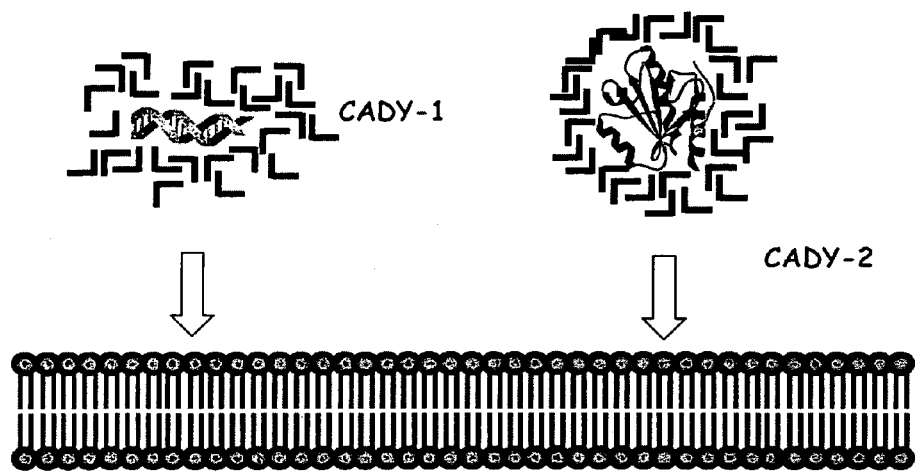

The present invention pertains to the field of intracellular delivery of molecules such as proteins or nucleic acids. In particular, the invention relates to a new cell-penetrating peptide (CPP) family, which exhibits high efficiency and low toxicity.

Cellular internalization of large hydrophilic therapeutic agents such as proteins or nucleic acids is still a challenging task because of the presence of the plasma membrane, which constitutes an impermeable barrier for such molecules. In order to circumvent this problem, several methods of carrier-mediated delivery systems have been developed. Among them, much attention has recently been given to the use of peptide-based delivery systems. The use of peptides with cell-penetrating properties has several advantages, which are mainly due to the various modifications that can be done to the peptide sequence. This allows the engineering of carriers addressing different cellular subdomains and/or able to transport various types of cargoes.

Many CPPs were designed from sequences of membrane-interacting proteins such as fusion proteins, signal peptides, transmembrane domains and antimicrobial peptides (Morris, Chaloin et al. 2000; Jarver and Langel 2004; El-Andaloussi, Holm et al. 2005). Within these sequences, short sequences called Protein Transduction Domains or PTDs proved to efficiently cross biological membranes without the need of a carrier or of a receptor, and to deliver peptides or proteins into intracellular compartments. Many investigations suggested that the use of PTD-based peptides could be of major importance for therapies against viral diseases or cancers. Among these, the third helix of the homeodomain of antennapedia called penetratin (Joliot and Prochiantz 2004), the Tat peptide derived from the transactivating protein Tat of HIV-1 (Wadia and Dowdy 2002), transportan (Pooga, Hallbrink et al. 1998) and VP22 (Elliott and O'Hare 1997) were used to improve the cellular uptake of peptides, proteins or oligonucleotides.

A second category of cell-penetrating peptides, designated as amphipathic peptides, has been described. An amphipathic molecule can be defined, in short, as consisting of two domains: a hydrophilic (polar) domain and a hydrophobic (non-polar) domain. For peptides, the amphipathic character can arise either from the primary structure, or from the secondary structure. Primary amphipathic peptides can be defined as the sequential assembly of a domain of hydrophobic residues with a domain of hydrophilic residues. Secondary amphipathic peptides are generated by the conformational state which allows the positioning of the hydrophobic and hydrophilic residues on opposite sides of the molecule.

Other peptides, such as polyarginine-based peptides, calcitonin-derived peptides, and oligomers, have also been proposed as tools for intracellular delivery of therapeutics.

Deshayes et al. have reviewed the available data concerning the use of the above-mentioned cell-penetrating peptides for delivering molecules into cells (Deshayes, Morris et al. 2005). It appears that the current vectors are limited, because of their lack of efficiency and/or their toxicity, and that little is known about the pathway of their cellular uptake, which constitutes a handicap for improving their efficiency.

The present invention pertains to a new family of cell-penetrating peptides having particularly advantageous properties.

A first aspect of the present invention is hence a cell-penetrating peptide which comprises an amino acid sequence consisting of $GLX_9RAX_9RX_1LX_2RSLX_9X_3X_4X_5X_6X_7X_8$ (SEQ ID No: 1), wherein $X_1$ is A, L or G, $X_2$ is W or none, $X_3$ is R or K, $X_4$ is K, L or S, $X_5$ is L or K, $X_6$ is R or W, $X_7$ is K or S, $X_8$ is A, V or Q, and $X_9$ is W, F or Y. According to the invention, $X_9$ can also be another aromatic chemical group. In a preferred embodiment of the invention, $X_9$ is W, which means that the cell-penetrating peptide comprises an amino acid sequence consisting of $GLWRAWRX_1LX_2RSLWX_3X_4X_5X_6X_7X_8$ (SEQ ID No: 25), with $X_1$ to $X_8$ as described above. The CPPs according to the invention have a secondary amphipathic structure. In the CPPs according to the invention, the amino acids can be either L- or D-amino acids.

In the present text, a "cell-penetrating peptide", also called a "peptide carrier", is a molecule, the core of which is a peptide. Other chemical groups can however be covalently bound to said peptidic core, in order to improve the overall stability of the molecule, and/or to provide it with additional properties, such as targeting ability. For example, a cell-penetrating peptide according to the invention can further comprise, covalently linked to the C-terminal extremity of the peptidic core of SEQ ID No: 1, one or several groups chosen amongst a cysteamide, a cysteine, a thiol, an amide, a carboxyl, a linear or ramified $C_1$-$C_6$ alkyl optionally substituted, a primary or secondary amine, an osidic derivative, a lipid, a phospholipid, a fatty acid, a cholesterol, a poly-ethylene glycol, a nuclear localization signal (NLS), and/or a targeting molecule. Alternatively or additionally, the cell-penetrating peptide of the invention can also comprise, covalently linked to the N-terminal end of the peptidic core of SEQ ID No: 1, one or several chemical entities chosen amongst an acetyl, a fatty acid, a cholesterol, a poly-ethylene glycol, a nuclear localization signal, and/or a targeting molecule. If necessary, for example in the case of N-terminal addition of cholesterol, a peptidic bridge can be used to bind a non-peptidic molecule to the peptidic core of the CPP. An example of such a bridge is —$CA_\beta$-.

Although some of the entities which can be covalently bound to the peptide of SEQ ID No: 1 comprise amino acids, the invention does not encompass every peptide or protein comprising SEQ ID No: 1, whatever the amino acids surrounding the core sequence of SEQ ID No: 1. Indeed, the only additional amino acid sequences that can be bound to a CPP according to the invention are the following:

(i) a peptidic bridge such as $CA_\beta$: the size of such a bridge will never exceed 5 amino acids. Preferably, the bridge consists of 1, 2 or 3 amino acids.

(ii) a nuclear localization signal (NLS): such signals are well known in the scientific literature. An example of NLS that can be used according to the present invention is PKKKRKV (SEQ ID No: 27). Other NLS which can be used can contain up to 11 amino acid residues, in the case of a bipartite NLS (Morris, Chaloin et al. 2002).

(iii) targeting peptides: targeting molecules which can advantageously be bound to the CPPs according to the invention, can be of peptidic nature. Examples of targeting peptides are epitopes, antibody fragments (Fab) which specifically target tissues or cell surface components or receptors, and the like. Whatever the molecules bound to the peptidic core of SEQ ID No: 1, CPPs according to the invention must retain their vector efficiency, i.e., their ability (i) to interact with the cargo, and (ii) to deliver said cargo into the cells. Therefore, in the context of the present invention, the sequence of a targeting peptide will preferably be no longer than 15 amino acids. A examples of such peptides are the RGD motif, NGR, transferrine, antibody fragments, and any of the peptides listed in Table 1 of the review by Allen (Allen 2002).

Apart from the targeting peptides, other targeting molecules can be bound to the CPPs of the invention, in order to obtain a specific delivery of molecules to particular cell types and/or organs. For example, sugars, such as monosaccharides (ex: glucose, galactose, glucosamine ou galactosamine), oligosaccharides, polysaccharides, or their analogues, as well as some oligonucleotides, or some organic molecules such as folate, can be used to that aim. Their targeting activity is due to the fact that they are recognized as ligands by some receptors which are over-expressed at the surface of cells in the zone of interest.

In a particular embodiment of the cell-penetrating peptide according to the invention, the amino acid sequence of the peptidic core is chosen in the group consisting of

```
GLWRALWRLLRSLWRLLWKA;       (SEQ ID No: 2)

GLWRALWRALWRSLWKLKRKV;      (SEQ ID No: 3)

GLWRALWRALRSLWKLKRKV;       (SEQ ID No: 4)

GLWRALWRGLRSLWKLKRKV;       (SEQ ID No: 5)

GLWRALWRGLRSLWKKKRKV;       (SEQ ID No: 6)

GLWRALWRLLRSLWRLLWKA;       (SEQ ID No: 7)

GLWRALWRALWRSLWKLKWKV;      (SEQ ID No: 8)

GLWRALWRALWRSLWKSKRKV;      (SEQ ID No: 9)

GLWRALWRALWRSLWKKKRKV;      (SEQ ID No: 10)
and

GLWRALWRLLRSLWRLLWSQ.       (SEQ ID No: 11)
```

Preferred cell-penetrating peptides according to the invention are CADY-1 (Ac-GLWRALWRLLRSLWRLLWKA-Cya) SEQ ID NO: 7; and CADY-2 (Ac-GLWRALWRAL-WRSLWKLKWKV-Cya) SEQ ID NO: 8.

Another aspect of the present invention is a complex comprising a cell-penetrating peptide as described above, and a cargo selected amongst nucleic acids, peptides, proteins, contrast agents, and toxins.

In a particular embodiment of the complexes of the invention, the cargo is a siRNA selected to silence a target mRNA. In this embodiment, the amino acid sequence of (core of) the cell-penetrating peptide preferably is GLWRAWRX$_1$LX$_2$RSLWX$_3$X$_4$X$_4$X$_5$KX$_6$ (SEQ ID No: 26), wherein X$_1$ is A, L or G, X$_2$ is W or none, X$_3$ is R or K, X$_4$ is K or L, X$_5$ is R or W, X$_6$ is A or V. For example, the amino acid sequence of the cell-penetrating peptide is chosen in the group consisting of:

```
GLWRALWRLLRSLWRLLWKA;       (SEQ ID No: 2)

GLWRALWRALWRSLWKLKRKV;      (SEQ ID No: 3)

GLWRALWRALRSLWKLKRKV;       (SEQ ID No: 4)

GLWRALWRGLRSLWKLKRKV;       (SEQ ID No: 5)

GLWRALWRGLRSLWKKKRKV;       (SEQ ID No: 6)
and

GLWRALWRGLRSLWKKKRKV.       (SEQ ID No: 7)
```

According to the invention, preferred CPPs for siRNA delivery have an amino acid sequence corresponding to SEQ ID Nos 2, 6 or 7.

In another embodiment of the complexes of the invention, the cargo is a peptide or a protein. In this embodiment, the amino acid sequence of (core of) the cell-penetrating peptide is SEQ ID No: 1, as described above, preferably with the proviso that X$_1$ is not G and X$_8$ is not A. Examples of amino acid sequences of cell-penetrating peptides that can be incorporated in complexes with peptides or proteins are the following:

```
GLWRALWRALWRSLWKLKWKV          (SEQ ID No: 8)

GLWRALWRALWRSLWKSKRKV          (SEQ ID No: 9)

GLWRALWRALWRSLWKKKRKV          (SEQ ID No: 10)

GLWRALWRALWRSLWKLKRKV          (SEQ ID No: 3)

GLWRALWRLLRSLWRLLWSQ           (SEQ ID No: 11)

GLWRALWRLLRSLWRLLWSQPKKKRKV    (SEQ ID No: 12)
```

According to the invention, preferred CPPs for proteins and peptide delivery have an amino acid sequence corresponding to SEQ ID Nos 8, 9 or 10. Depending on the cargo and the application, the skilled artisan can use the intracellular targeting properties of those CPPs, especially those of SEQ ID Nos 8 and 9, which target the nucleus and the cytoplasm, respectively.

Of course, the cell-penetrating peptides comprised in the complexes according to the invention can be modified as mentioned above, by binding additional molecules to the N-terminal and/or the C-terminal ends of their peptidic core of SEQ ID No: 1. In a preferred embodiment of such complexes, the cell-penetrating peptide comprises an acetyl group covalently linked to its N-terminus, and/or a cysteamide group covalently linked to its C-terminus. Alternatively or additionally, the cell-penetrating peptide further comprises a cholesterol molecule, covalently linked to its C-terminus or its N-terminus. When bound to the N-terminus, the cholesterol molecule can be linked via a bridge as described above, for example a CA$_β$ bridge.

The inventors have investigated various parameters in order to optimize the cargo delivery, and have found that when the size of the complexes is <500 nm, the mechanism of cellular uptake of said complexes is independent on the endosomal pathway. Hence, the size of the complexes according to the invention is preferably between 50 and 300 nm and, more preferably, between 100 and 200 nm. This corresponds, for siRNA/CADY complexes, to a ratio of 1/20 to 1/25.

According to an advantageous embodiment of the complex according to the invention, at least part of the cell-penetrating peptides are bound to a targeting molecule. As mentioned above, a targeting molecule can be a peptide, a sugar, etc. When only part of the CPPs are initially bound to a targeting molecule, this latter can be chosen bigger than the maximal size of targeting molecules which are acceptable when all the CPPs are bound to targeting molecules. The targeting molecule can be either covalently linked to a CPP, or bound to the complex via non-covalent bounds. In some cases, the cargo itself can be a targeting molecule, especially for targeting tumor cells.

A therapeutic composition comprising a complex as described above is, of course, part of the present invention.

In one particular aspect, the invention pertains to the use of a cell-penetrating peptide, or of a complex as described above, for the preparation of a therapeutic composition for use in anticancer therapy. For example, a therapeutic composition according to the invention comprises anti-cyclin B1 siRNA/CADY complexes, and/or p1p27/CADY complexes, and/or pRXL/CADY complexes.

The invention also pertains to a method for delivering a molecule into a cell in vitro, comprising a step of putting said cell into contact with a complex comprising said molecule and cell-penetrating peptides as described above.

The invention is further illustrated by the following figures and examples.

LEGENDS TO THE FIGURES

FIG. 1: Schematic representation of CADY cellular uptake mechanism.

Figure 2:
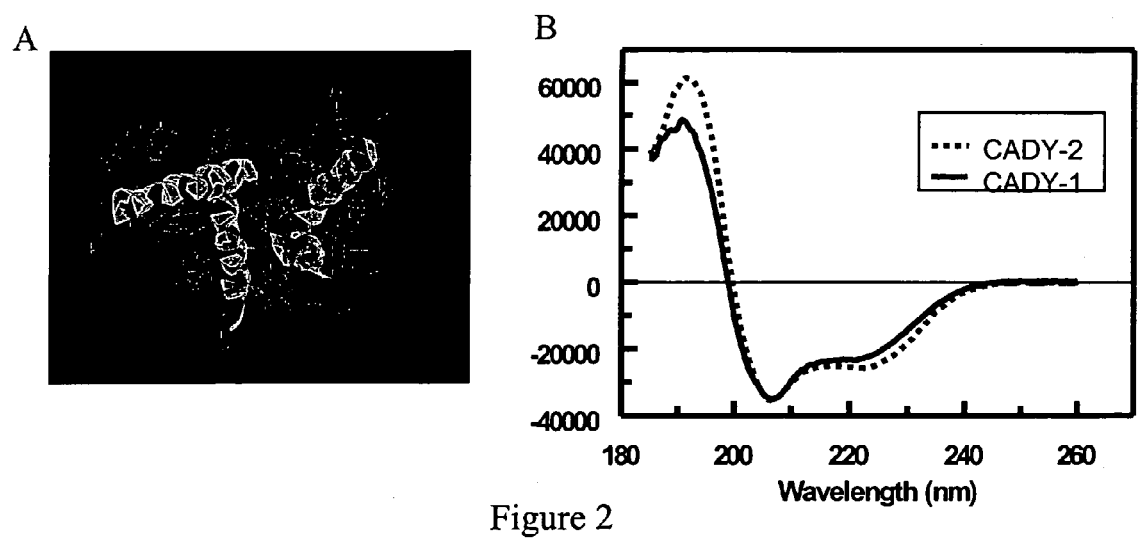

FIG. 2: Structure of CADY in the interaction with the membrane.

(A) modelisation (B) CD experiments—Far UV CD spectra were recorded on a JASCO J-810 spectro-polarimeter (JASCO Corporation, Tokyo, Japan) using a quartz cuvette with a path length of 1 mm. Spectra were corrected from the baseline buffer spectrum and smoothed with the JASCO software. Peptides were dissolved to a fixed concentration of 50 µM in water or in PBS. CD spectra were collected at 23° C. and each spectrum represents the average of 4 scans. CADY-1 & CADY-2 adopt a α-helical structure characterized by two minima at 208 nm and 222 nm, respectively.

Figure 3:
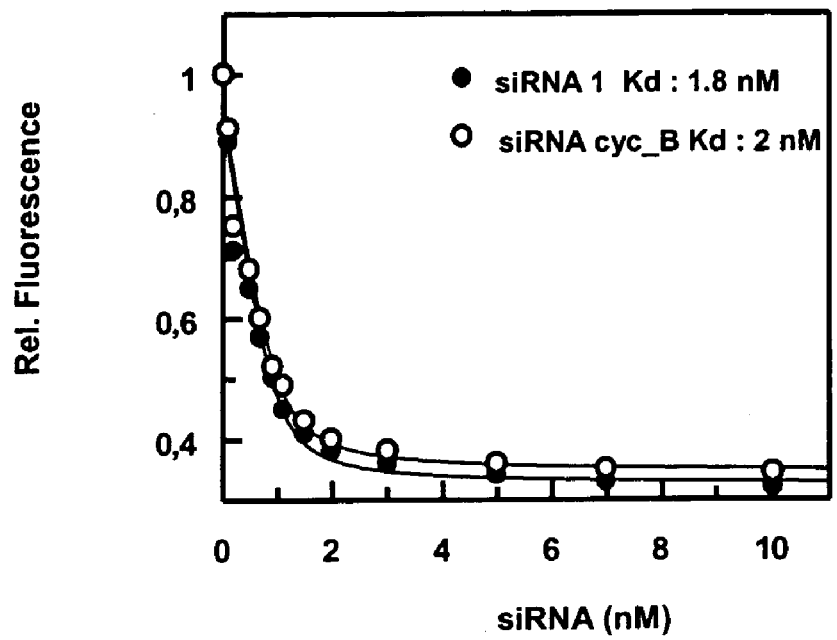
Figure 3:
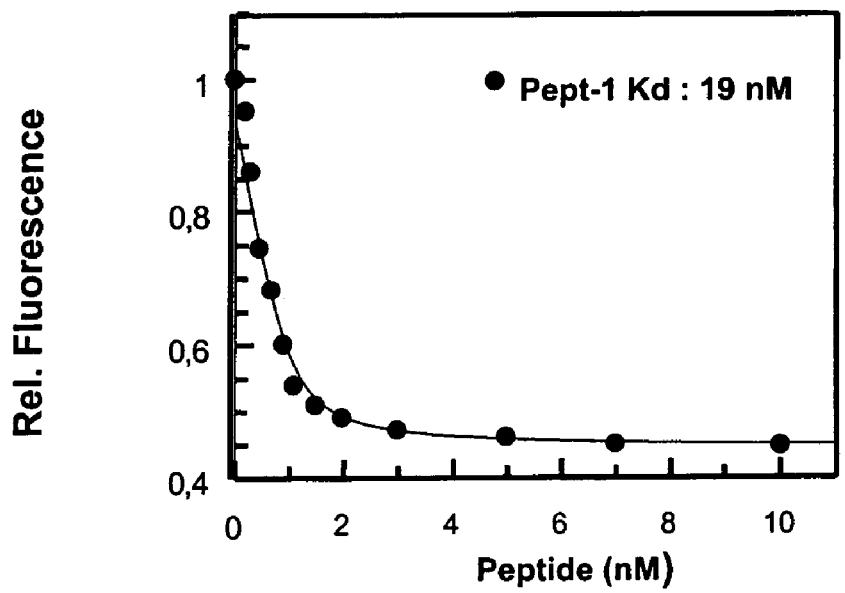

FIG. 3: Formation of CADY/cargo complexes.

Binding of cargoes to CADY was monitored by steady state fluorescence spectroscopy. The intrinsic fluorescence associated to the Trp residues of CADY was used as sensitive probe. The fluorescence of CADY is centered at 340 nm upon excitation at 290 nm. Experiments were performed in phosphate buffer (PBS). A fixed concentration of CADY (0.1 µM) was titrated by increasing concentrations of cargoes.

(A) For the experiments with CADY-1, two different siRNAs (double stranded RNA) targeting cyclin B1 and GAPDH, were used.

(B) For the experiment with CADY-2, a short 17-residues peptide was used.

Figure 4:
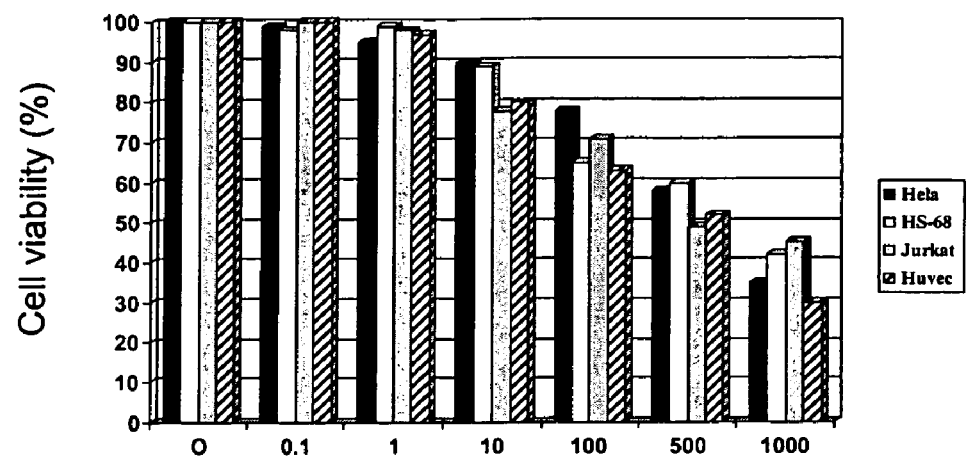
Figure 4:
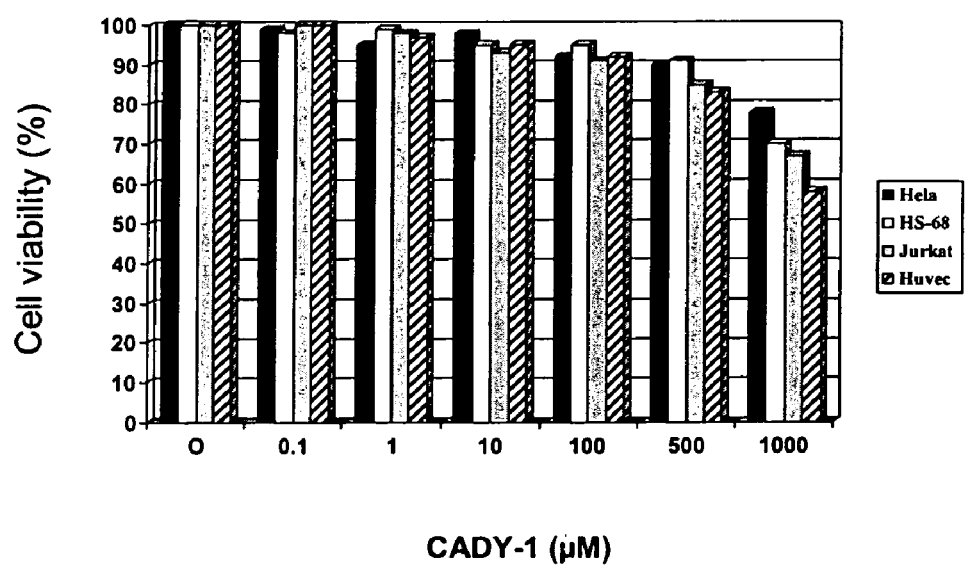

FIG. 4: Toxicity of CADY peptides.

Cells were incubated in the presence of increasing concentrations (from 0.1 µM to 1 mM) of CADY-1, either alone (A) or in complexes with a cargo siRNA at a ratio of 1/20 (B). Cell viability was estimated using MTT assay, after 12 hrs of incubation.

Figure 5:
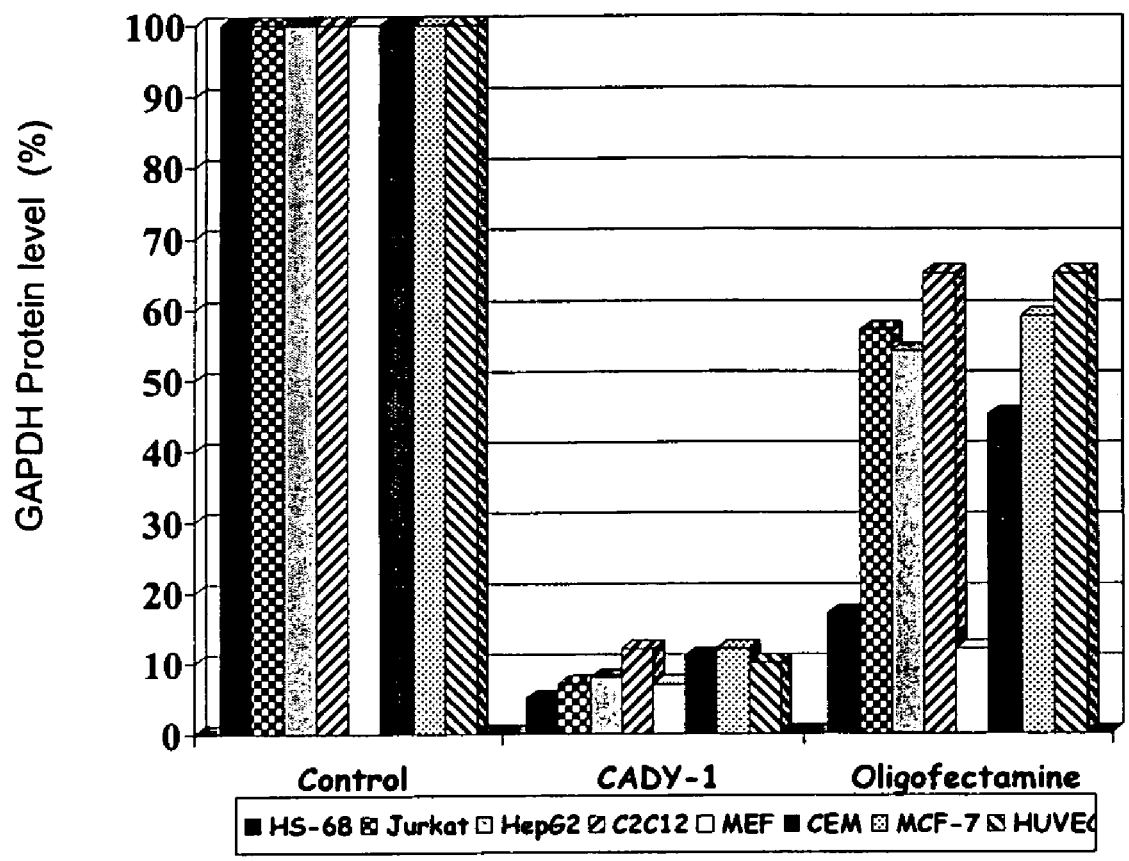

FIG. 5: CADY-1-mediated delivery of siRNA.

The different cell lines were cultured as described in the ATCC protocol. Cell lines were cultured in Dulbecco's Modified Eagle's Medium supplemented with 2 mM glutamine, 1% antibiotics (streptomycin 10000 µg/ml, penicillin, 10000 IU/ml) and 10% (w/v) fetal calf serum (FCS), at 37° C. in a humidified atmosphere containing 5% $CO_2$. CADY/siRNA complexes were formed by incubation of siRNA (50 nM) with CADY at a molecular ratio of 1:20 (i.e., one molecule of siRNA for 20 molecules of CADY), in 500 µl of DMEM for 30 min at 37° C. Cells grown to 40 to 60% confluence were then overlaid with preformed complexes. After 30 min incubation at 37° C., 1 ml of fresh DMEM supplemented with 10% fetal calf serum was added directly to the cells, without removing the overlay of CADY/siRNA complexes, and cells were returned to the incubator. Control experiments were performed with siRNA (50 nM) transfected with cationic lipids Oligofectamine (Invitrogen, Carlsbad, US), according to the guidelines of the manufacturer. A well established siRNA targeting GAPDH protein (Ambion-CA) was used as cargo. The knockdown of the GAPDH at the protein level was quantified 48 hrs after transfection by Western blot analysis using polyclonal antibody (Ref. ABCAM GAPDH antibody—ab9385 rabbit polyclonal). The percentage of GAPDH knockdown was estimated by comparison with control essays using a mismatch siRNA delivered with CADY at the same molecular ratio. Data are the average of 4 separated experiments.

Figure 6:
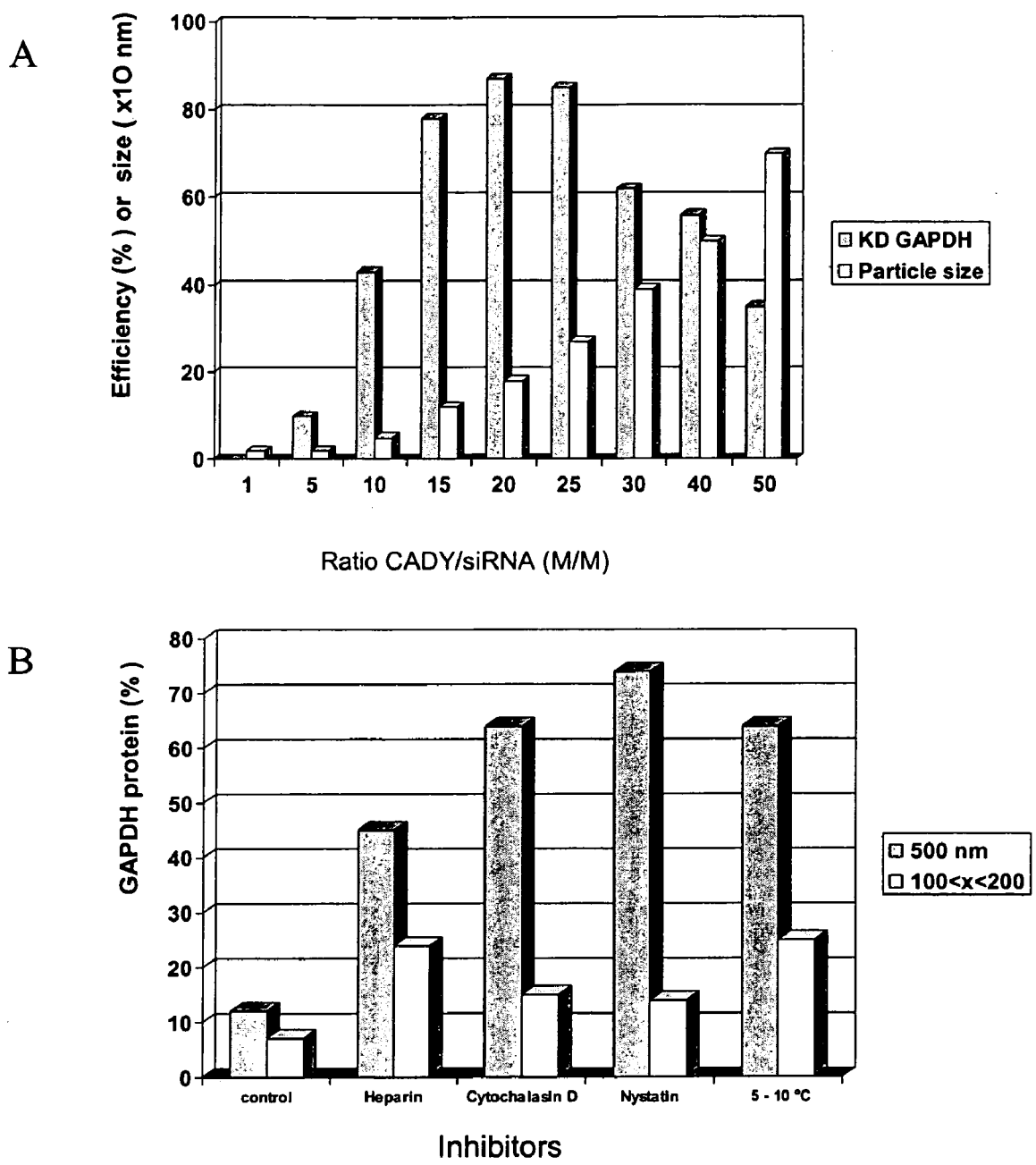

FIG. 6: Mechanism of cellular uptake of CADY.

(A) impact of both the size of the particle and of the molar ratio CADY/siRNA on the efficiency of the siRNA. CADY/siRNA-GAPDH complexes were formed by incubation of siRNA (50 nM) with increasing molecular ratio of CADY from 5:1 to 50:1. Experiments were performed on Human HS-68 fibroblasts or Hela cell lines. The size of the particle was determined by light scattering and the knock down of GAPDH protein was quantified by Western blot analysis.

(B) role of the endosomal pathway on the efficiency of CADY-mediated siRNA delivery. CADY/siRNA-GAPDH complexes were formed by incubation of a fixed concentration of siRNA (50 nM) with CADY-1 at two molar ratios: 20:1 and 50:1, which correspond to CADY/siRNA-GAPDH particles of 100-200 nm and of 500 nm diameter size, respectively. In order to determine the cellular uptake mechanism of CADY, the transfection experiments were performed in the presence of different inhibitors of the endosomal pathway, as previously described by Dowdy and colleagues (Wadia, Stan et al. 2004). The following inhibitors of the endosomal pathway were used: Heparin (20 µg/ml), Nystatin or Filipin (25 µg/ml), Cytochalasin D (5 µM). The cells were incubated in the presence of the inhibitor one hour prior transfection; the inhibitor was then maintained in the culture medium for one hour after transfection. Cells were then extensively washed, trypsine was added in order to remove any CADY/siRNA complex associated to the cell membrane. Cells were the cultured for 24 additional hours. Experiments were performed on HS-68 fibroblasts or Hela cell lines. The knock down of GAPDH protein was quantified by Western blot analysis.

Figure 7:
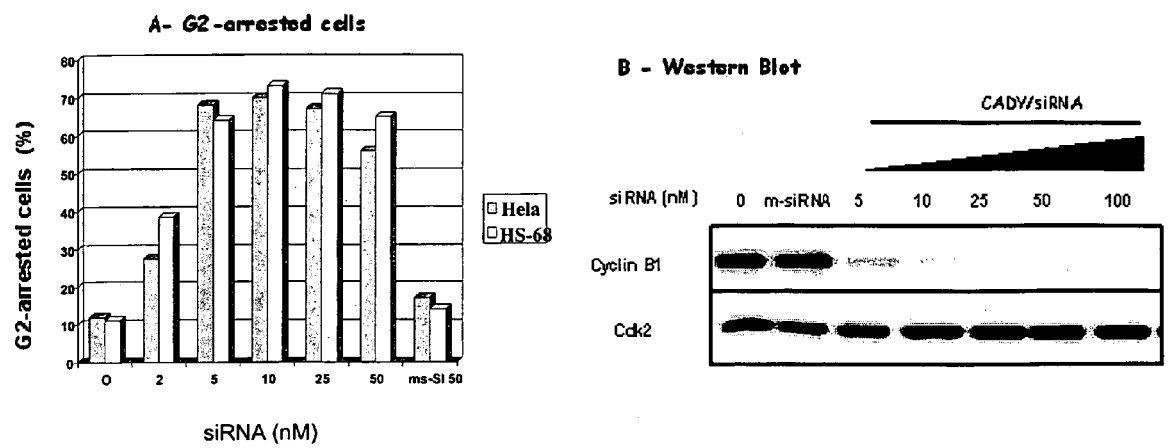

FIG. 7: CADY-mediated cyclin-B1 siRNA delivery

The effect of increasing concentrations of siRNA from 2 nM to 100 nM complexed with CADY (ratio 1/20) on cyclin B1 protein levels was analyzed in several cell lines (Hela cells, human fibroblasts (HS 68) and 293 cells). A stock solution of CADY/siRNA formulation was prepared using a siRNA concentration of 100 nM associated with a CADY-1 at a molar ratio of 1/20. Lower concentrations of formulated siRNA (from 50 nM to 0.5 nM) were obtained by serial dilution of the stock solution in PBS, in order to maintain the siRNA/CADY ratio, and therefore the size of the particle around 200 nm diameter. SiRNA/CADY complexes were overlaid onto asynchronous cultured cells in the presence of FBS (10%).

(A) The effect of Cyclin B1 siRNA was monitored on cell cycle progression by FACS analysis 30 hrs after transduction.

(B) Cyclin B1 protein levels were quantified by Western blotting 30 hrs after transduction. To that aim, cells were collected and proteins were separated on SDS gel (12%), then transferred onto nitro-cellulose for Western blotting. Mouse monoclonal anti-Cyclin B1 antibodies (SC-245) and rabbit polyclonal anti-Cdk2 antibodies (SC-163) for Western blotting were obtained from Santa Cruz Biotechnology Inc., (Santa cruz, CA). Cdk2 protein kinase was used as a control to normalize protein levels.

Figure 8:
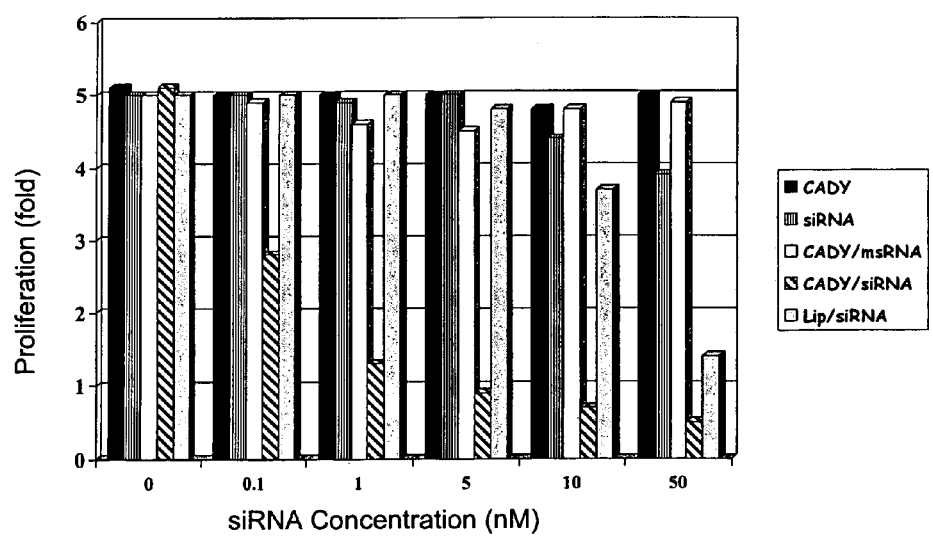

FIG. 8: potency of CADY/siRNA complex to block cancer cell proliferation.

Experiments were performed on MCF-7 or U2OS cells. Cells were treated on day 1 with different concentrations of siRNA and CADY/siRNA complexes (0.1 to 50 nM). A stock solution of CADY/siRNA formulation was prepared using a siRNA concentration of 100 nM associated with a CADY-1 at a molar ratio of 1:20. Lower concentrations of formulated siRNA (from 50 nM to 0.5 nM) were obtained by serial dilution of the stock solution in PBS, in order to maintain the siRNA/CADY ratio and therefore the size of the particle around 200 nm diameter. Mismatched siRNA and free CADY were used as controls, and Oligofectamine (Invitrogen, USA) was used as lipid-based control delivery agent (manufacturer protocol). The inhibition of cell proliferation was determined after 7 days.

Figure 9:
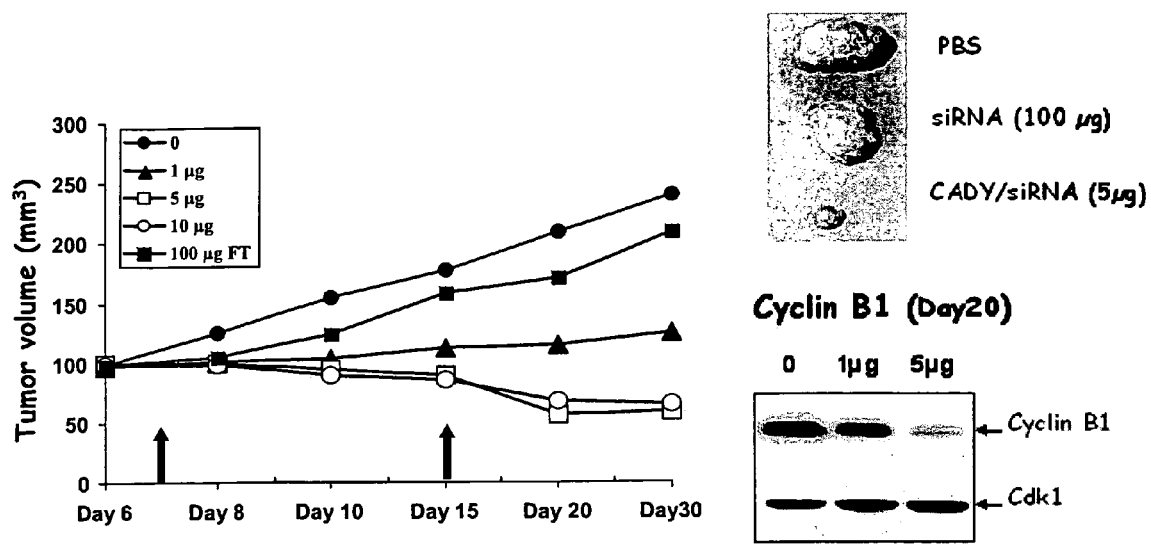

FIG. 9: intratumoral injection of anti-cyclin B1/CADY complexes

The effect of the anti-cyclin B1 siRNA was investigated on a tumor animal model, using Swiss nude mice, injected subcutaneously with $2 \times 10^7$ 15PC3 cells, A549 cells (human bronchoalveolar carcinoma) or HER2 cells. Different CADY/siRNA complexes were injected directly into the tumor (100 µl) at day 7 and at day 15. siRNA/CADY complexes were obtained as described before at a ratio 1:20. The size of the tumor was measured every 2 days and the level of cyclin B1 protein was determined at Day 20 by Western blot analysis. Results correspond to the average of 5 different animals.

Figure 10:
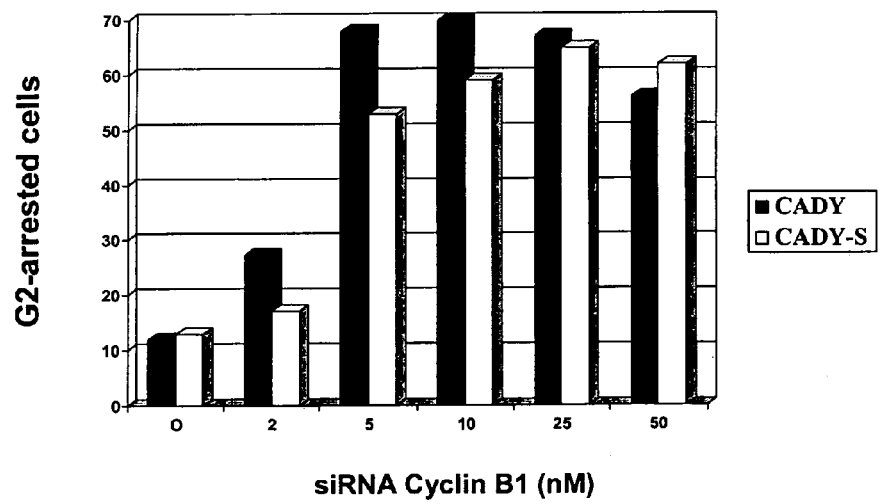

FIG. 10: Comparison of CADY versus CADY-S

The efficiencies of CADY-1 and CADY-S vectors for delivering anti-cyclin B1 siRNA were compared on Hela/HS68 cells, using the same assay as described in the legend of FIG. 7A. The figure shows the results obtained on HS68 fibroblasts with a CADY-1 vector devoid of cholesterol.

Figure 11:
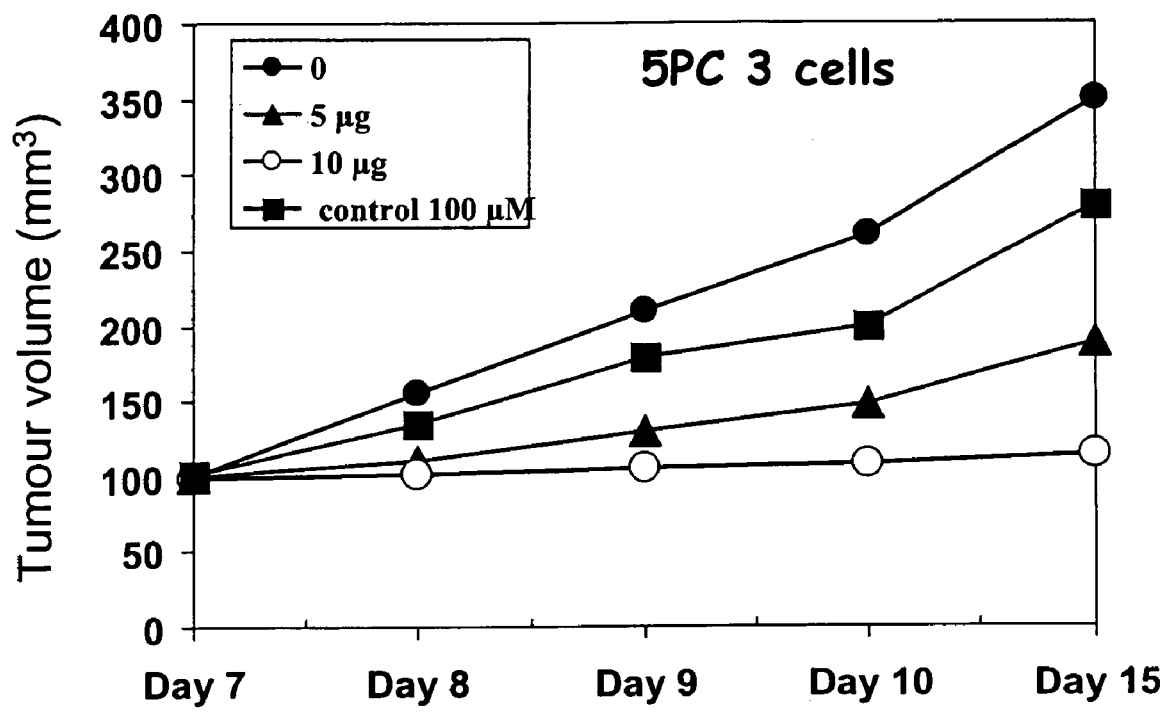
Figure 11:
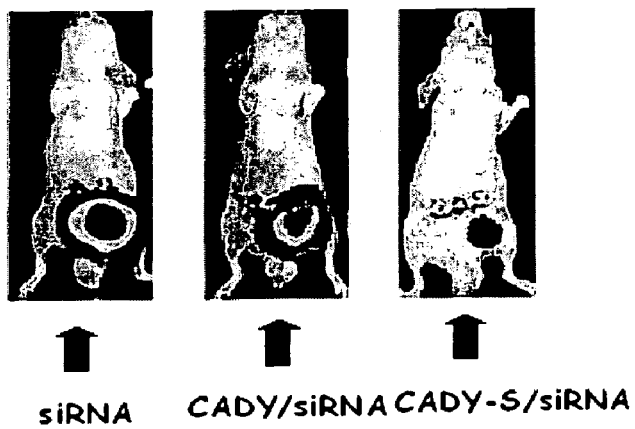

FIG. 11: CADY-S-mediated delivery of anti-cyclin B1 siRNA through intravenous injection to block tumor growth in vivo Experiments were performed on two tumor mouse models.

(A) $1 \times 10^6$ 5PC3 adenocarcinoma cells were injected subcutaneously into the flanks of NCR nude mice (day 1). siRNA/CADY-S complexes were obtained as described before at a ratio 1:20. CADY-S/siRNA complexes were injected intravenously at day 7. The size of the tumor was measured every day. Results correspond to the average of 5 different animals.

(B) $1 \times 10^6$ tumor cells expressing luciferase were injected intraperitoneally in the mice (4 to 8 week-old immune competent A/J female mices). Tumors were monitored using in vivo Imaging System (IVIS-Xenogen), which quantified total body bioluminescence after injection of D-luciferin. The tumor cells are visualized on three mice, each representative of one group (siRNA alone, CADY/siRNA complexes, and CADY-S/siRNA complexes).

Figure 12:
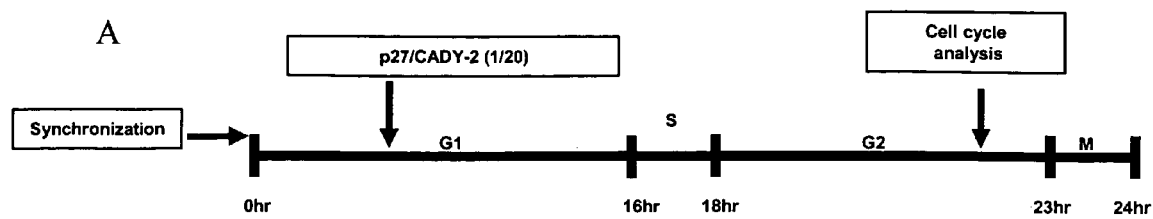
Figure 12:
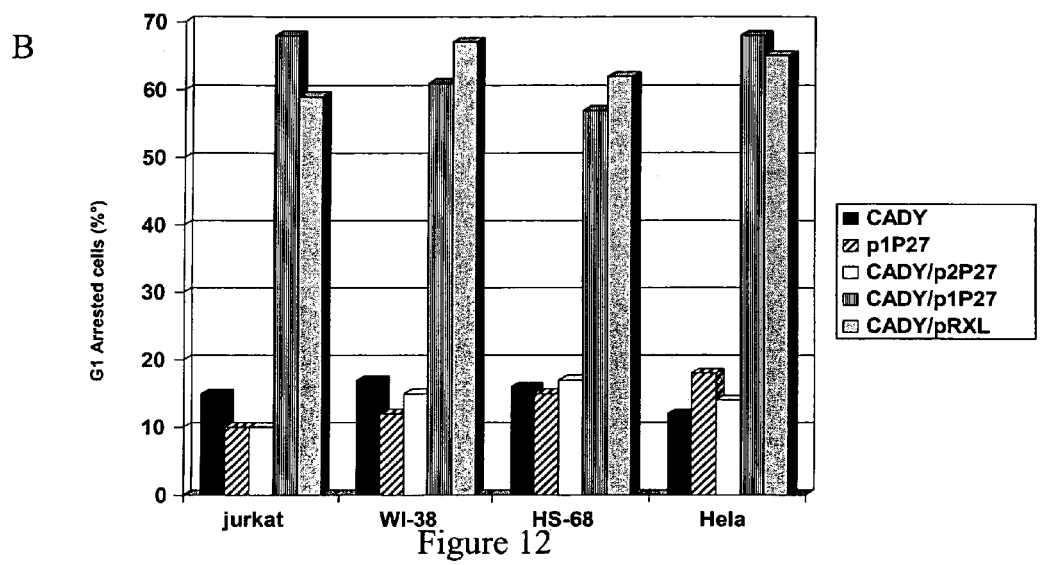

FIG. 12: The different p27-derived peptides were associated with CADY-2 at a molar ratio of 1/20, since it was determined that at this ratio, the average size of the particle is of about 100-200 nm in diameter. The formulations were obtained in phosphate buffer, using a fixed concentration of peptide of 1 µM. Cell lines were cultured in Dulbecco's Modified Eagle's Medium supplemented with 2 mM glutamine, 1% antibiotics (streptomycin 10'000 µg/ml, penicillin, 10'000 IU/ml) and 10% (w/v) fetal calf serum (FCS), at 37° C. in a humidified atmosphere containing 5% $CO_2$. Cells were synchronized by serum privation during 40 hrs, and cultured in Dulbecco's Modified Eagle's Medium supplemented with 2 mM glutamine, 1% antibiotics. G1 synchronized cells were released upon serum addition, then overlaid with preformed CADY-2/peptide complexes. After 30 min incubation at 37° C., 1 ml of fresh DMEM supplemented with 10% fetal calf serum was added directly to the cells, without removing the overlay of CADY/peptide complexes, and cells were returned to the incubator. The level of cell arrest in G1 was analyzed by FACS 24 hrs after release.

(A) Protocol (B) Results obtained with Jurkat, WI-38, HS-68 and HeLa cells.

Figure 13:
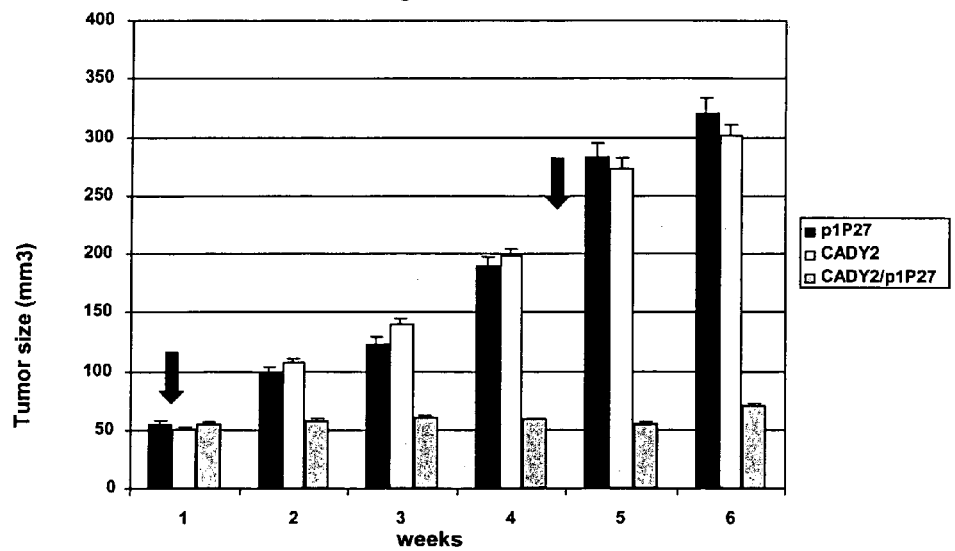

FIG. 13: Effect of p1p27/CADY complexes on tumor growth in vivo

The tumor animal model consists of Swiss nude mice, injected subcutaneously with $2 \times 10^7$ Human H1299 adenocarcinoma cells. CADY2/p1p27complex and free CADY-2 and peptides were injected directly into the tumor (100-300 µg) after 1 and 4 weeks. p1p27/CADY complexes were obtained as described before at a ratio 1/20. Controls were performed by injecting PBS, CADY alone, or naked p1p27 instead of the p1p27/CADY-2 complex. The size of the tumor volume was measured with calipers once a week. Results correspond to the average of 5 different animals.

EXAMPLES

Example 1

Peptide Synthesis

Several peptides were synthesized, and selected for their ability to deliver different kinds of cargoes, especially siRNA (CADY-1 family) and peptides or proteins (CADY-2 family).

CADY-1 peptides have been designed so that charges are well distributed all over the vector. They have been selected for their ability to deliver an anti-GAPDH siRNA into HeLa or HS-68 cultured cells, with an efficiency sufficient to obtain at least a 50% decrease of GAPDH protein level after 24 hrs of incubation with 50 nM siRNA. The efficiency of expression inhibition was determined using CADY-1 (SEQ ID No: 2) as a reference, since this peptide enables a 95% inhibition.

An important parameter for designing CADY-2 peptides is the presence of tryptophane residues, and their repartition in the peptide. The CPPs have been selected using the p1p27 peptide (described below) as test cargo. The delivery efficiency was functionally determined by measuring the G1 arrest of synchronized HeLa or HS68 cells, after 24 hrs of incubation in the presence of 200 nM p1p27 peptide. The CADY-2 reference peptide is CADY-2 (SEQ ID No: 8), which leads to 75% of cells arrested in G1.

```
       CADY-1 vectors for siRNA delivery (SEQ ID No: 2)
CADY-1:     GLWRALWRLLRSLWRLLWKA-Cya (SEQ ID No: 3)
CADY-1b:    GLWRALWRALWRSLWKLKRKV-Cya (SEQ ID No: 4)
CADY-1c:    GLWRALWRALRSLWKLKRKV-Cya (SEQ ID No: 5)
CADY-1d:    GLWRALWRGLRSLWKLKRKV-Cya (SEQ ID No: 6)
CADY-1e:    GLWRALWRGLRSLWKKKRKV-Cya (SEQ ID No: 7)
CADY-1S:    Cholesterol-GLWRALWRLLRSLWRLLWKA
```

-continued

```
                                            (SEQ ID No: 13)
CADY-1S1:   Cholesterol-CAβ-GLWRALWRLLRSLWRLLWKA (SEQ ID No: 7)
CADY-1S2:   GLWRALWRLLRSLWRLLWKA-Cholesterol CADY-2 vector for peptide/protein delivery (SEQ ID No: 8)
CADY-2:     GLWRALWRALWRSLWKLKWKV-Cya (SEQ ID No: 9)
CADY-2b:    GLWRALWRALWRSLWKSKRKV-Cya (SEQ ID No: 10)
CADY-2c:    GLWRALWRALWRSLWKKKRKV-Cya (SEQ ID No: 3)
CADY-2d/1b: GLWRALWRALWRSLWKLKRKV-Cya (SEQ ID No: 12)
CADY-2e:    GLWRALWRLLRSLWRLLWSQ-PKKKRKV-Cya
```

The N-terminal extremity of these peptides is linked to an acetyl group when no further indication appears. It can also be linked to a cholesterol molecule (when indicated), which is either linked directly to the N-terminus, or linked to the vector through a $CA_\beta$ bridge, which changes the relative orientation of the cholesterol and the core of the vector (wherein the "core of the vector" designates the peptidic part of the vector of SEQ ID No:1).

The C-terminal extremity is linked either to a cholesterol molecule (CADY-S2) or to a cysteamide group (i.e., CO—NH—CH2—CH2—SH).

Peptide synthesis was carried out at a 0.2 mmol scale, starting from a Fmoc-PAL-PEG-PS resin, using a Fmoc-continuous flow peptide synthesis instrument (Pioneer™, Applied Biosystems, Foster City, Calif.). The coupling reactions were performed with 0.5 M of HATU (2-(7-Aza-1H-benzotriazole-1-yl)-1,1,3,3-tetramethyluronium hexafluorophosphate) in the presence of 1 M of DIEA (diisopropylethylamine). Recoupling was carried out at positions: 6, 7, 10, 11, 13, 14, 17 and 18. Protecting group removal and final cleavage from the resin were carried out with TFA (trifluoroacetic acid)/EDT (ethanedithiol)/thioanisole/phenol/$H_2O$ (82.5/2.5/5/5/5%) during 5 h 30 min. The reaction mixture was then filtered through a cotton filter in cold diethyl ether. Since there occurred no peptide precipitation, ether was removed under rotary evaporation to obtain a yellow oil. Neat ether was added to the oil and stored at −20° C. overnight to allow the peptide to precipitate. A certain quantity of peptide has already precipitated in the cleavage cocktail (it is unusual for a peptide to precipitate in a near pure solution of TFA). This precipitate (+the cotton and the resin) was resuspended in $CH_3CN$ (containing 0.08% TFA) and $H_2O$. After filtration and thorough washes by $CH_3CN$/TFA and $H_2O$, the filtrate was lyophilized prior to purification.

The crude peptide was purified by RP-HPLC on a C18 column (Interchrom UP5 WOD/25M Uptispere 300 5 ODB, 250×21.2 mm). Electrospray ionization mass spectrum was in complete agreement with the proposed structure.

Example 2

Structure of CADY When Interacting with a Membrane

The structure of CADY peptides was investigated by spectroscopy. It was demonstrated by circular dichroïsm that CADY adopts a helical structure in water or in phosphate solution. CADY forms a secondary amphipathic organization. Helical structure of CADY results in a hydrophobic and a hydrophilic faces. Molecular dynamic analysis reveals that CADY forms multimeric structures, involving at least 4 CADY molecules within the membrane (FIGS. 1 and 2). FTIR measurement of transferred CADY/membrane have confirmed that CADY peptides form an helical structure in the membrane.

Example 3

CADY Forms Stable Particles with Cargoes Through Non Covalent Interactions

The inventors have investigated the formation of CADY/cargo complexes and demonstrated that CADY peptides are able to form stable complexes with their cargoes. CADY-1 interact mainly with siRNA (FIG. 3A) and CADY-2 mainly with peptides and proteins (FIG. 3B). Binding of cargoes to CADY was monitored by steady state fluorescence spectroscopy, using the intrinsic fluorescence associated to the Trp residue of CADY. For each CADY peptide, a fixed concentration of CADY was titrated by increasing concentration of cargoes. The binding of the cargo induced a marked quenching of fluorescence of both CADY peptides, and the dissociation constants were calculated from data fitting, using a quadratic equation which allows the determination of the ratio CADY/cargo. Dissociation constants and ratios were estimated to 2 nM for CADY-1/siRNA and 19 nM for CADY2/peptide, with a ratio at saturation of 1/10 and 1/20, respectively, whatever the variant of CADY-1 or CADY-2. However, cholesterol modification (i.e., addition) reduced 2 to 10 folds the affinity of CADY-1 for the siRNA. These results suggest that in both cases, more than one peptide interact with the cargo, and that both CADY-1 and CADY-2 are able to form particles with their respective cargoes.

Example 4

CADY Forms Stable and Non-Toxic Particles

The toxicity of CADY peptides has been investigated on different cell lines. Cells were incubated in the presence of increasing concentrations of CADY (from 0.1 µM to 1 mM) for 12 hrs and cell viability was estimated using MTT assay. Data reported in FIG. 4A demonstrated that CADY-1 is not toxic on the tested cell lines, up to a concentration of 100 µM, with a $EC_{50}$ of 0.5 mM.

The different CADY variants have been tested on HS-68 and Hela cells. The results are reported in the Table 1 below.

TABLE 1

| Peptides | free EC50 (mM) | complexed EC50 (mM) |
|---|---|---|
| CADY-1 | 0.4 | >2 |
| CADY-1b | 0.5 | >2 |
| CADY-1c | 0.45 | >2 |
| CADY-1d | 0.5 | >2 |
| CADY-1e | 0.34 | 1.5 |
| CADY-S | 0.2 | 1 |
| CADY-S2 | 0.25 | 0.8 |
| CADY-2 | 0.23 | 1 |
| CADY-2b | 0.28 | 0.9 |
| CADY-2c | 0.34 | 0.8 |
| CADY-2d | 0.38 | 1.5 |
| CADY-2e | 0.43 | >2 |

TABLE 1-continued

| Peptides | free EC50 (mM) | complexed EC50 (mM) |
|---|---|---|
| KALA | 0.07 | |
| GALA | 0.05 | |
| TAT | 0.1 | |
| Lipofectamine | 0.2 | |

The inventors demonstrated that association with cargo molecule (ratio 1/20) significantly reduced the toxicity of the carrier, an average $EC_{50}$ of 2 mM was calculated. The lack of toxicity of CADY/cargo complexes can be directly associated to absence of free carrier peptide in the solution (FIG. 4B). Lipofectamine and other membranolytic CPP (KALA, GALA, TAT), which exhibit more that 70% toxicity at concentration of 100 μM, were used as controls.

Example 5

CADY-Mediated Delivery of siRNA

The ability of CADY-1 and variants to deliver siRNA was evaluated on both adherent and suspension cell lines, using GAPDH as the target of siRNA.

siRNA targeting the 3'UTR of GAPDH were from the Silencer™ GAPDH siRNA kit (Ambion). Fluorescent labeling of siRNA was performed using either the Fam or the Cy3 Silencer™ labeling kit (Ambion) and modified as described in the manufacturer's protocol. pRL-Luc reporter gene was from Promega and siRNA targeting luciferase sense 5'-CUUACGCUGAGUACUUCGATT-3' (SEQ ID No: 14) and antisense 3'-TTGAAUGCGACUCAUGAAGCU-5' (SEQ ID No: 15) and mismatch sense 5'-CGUACGCGGAAUACU-UCGATT-3' (SEQ ID No: 16) and antisense 3'-TTG-CAUGCGCCUUAUGAAGCU-5' (SEQ ID No: 17) siRNA were obtained from Genset Oligos.

The results, presented in FIG. 5, show that CADY-1 is more efficient than the lipofectamine control. The percentage of GAPDH knockdown, estimated by comparison with a control essays using a mismatch siRNA delivered with CADY at the same molecular ratio, is also reported in Table 2 below. Data are the average of 4 separated experiments.

TABLE 2

| Cell lines | Knockdown |
|---|---|
| Hela | 85% |
| Jurkat | 80% |
| HepG2 | 70% |
| C2C12 | 70% |
| MEF | 70% |
| HS-68 | 80% |
| CEM-SS | 80% |
| U2OS | 75% |
| MCF7 | 70% |
| MT4 | 65% |
| HER2 | 60% |
| MDA-MB | 75% |
| Balb/c3T3 | 80% |

Example 6

Mechanism of Cellular Uptake of CADY-1

Whatever the CPP, the common major concern in the development of new PTD strategy is to avoid any endosomal pathway and/or to facilitate the escape of the cargoes from the early endosomes in order to limit their degradation. The cellular uptake mechanism of CADY-1 was therefore investigated in detail. The inventors demonstrated that, in contrast to most of the delivery systems described so far for siRNA, CADY-mediated delivery of active siRNA is independent of the endosomal pathway and directly correlated to the size of the particle CADY/siRNA.

Indeed, results reported in FIG. 6A revealed that efficiency of CADY is dependent on the size of the particle formed with siRNA. Optimal biological response was obtained for a CADY/siRNA ratio of 1:20 to 1:25, which corresponds to a nano particle (size of 100-200 nm). Therefore, calibration of the formulation is an essential parameter in the efficiency of CADY-1.

Results reported in FIG. 6B demonstrated that none of the tested inhibitors affected the cellular uptake of CADY and the associated siRNA biological response. In contrast to other CPP, the mechanism of cellular uptake of CADY/siRNA particle is independent of the endosomal pathway. However, the size of the particle and CADY/siRNA molar ratio need to be controlled, so that the diameter of the particles remains below 200 nm and the CADY/siRNA molar ratio remains under 1:25. In contrast, for particles of diameter >500 nm, the mechanism is partially associated to the endosomal pathway.

These data demonstrate that calibration of the formulation is an essential parameter in the efficiency of CADY-1, and that the optimal formulation for CADY/siRNA is: ratio 1:20 to 1:25 and nano particle (size of 100-200 mm).

Example 7

CADY-Mediated In Vitro Delivery of siRNA Targeting Cyclin-B1

Cell cycle progression is driven by sequential activation of essential heterodimeric protein kinase complexes (Cdk/cyclin complexes). Most of the drugs currently designed to target cell cycle progression are directed against the kinase activity of the Cdk subunits. However, as such drugs generally tend to affect other cellular kinases non specifically, the inventors have decided to target the regulatory cyclin subunit instead, as a more appropriate means of improving both the selectivity and the efficiency of cell cycle inhibitors. In particular, cyclin B1 constitutes a key target for cancer therapy, as a component of the essential "Mitosis Promoting Factor", together with protein kinase Cdk1.

A siRNA molecule was hence designed to target cyclin B1. The following siRNA sequence was selected out of 10 different sequences, and the oligonucleotides were obtained from proligo:

```
Si-Cyclin B sense:
5'-GGCGAAGAUCAACAUGGCATT-3'    (SEQ ID No: 18)

Si-Cyclin B antisense:
5'-UGCCAUGUUGAUCUUCGCCTT-3'    (SEQ ID No: 19)

Mismatch sense:
5'-GGUGAAGAUCAGCAUGGCATT-3'    (SEQ ID No: 20)

Mismatch antisense:
5'UGCCAUGUCGAUCUUCACCTT3'      (SEQ ID No: 21)
```

The potency of this siRNA was investigated using CADY as delivery system. The biological response of CADY-mediated delivery of siRNA targeting cyclin B1 was examined. To this aim, the inventors first assessed whether cyclin B1 protein levels were downregulated by CADY-mediated delivery of siRNA, and to what extent, compared to delivery of siRNA using classical lipid formulation.

As shown in FIG. 7A, delivery of siRNA cyclin B1 is associated to a cell cycle arrest in G2, characteristic of a knock down of the cyclin B1 protein. Western blot analysis confirmed that the observed G2-arrest is directly associated to a dramatic knock down of the cyclin B1 protein level (FIG. 7B). Interestingly, the G2 arrest is observed at low concentration of siRNA of 2 nM. This demonstrates the high potency of CADY for siRNA delivery and rapid release into the cytoplasm. Using CADY-mediated delivery can hence enable a significant response with only low concentrations of siRNA, which will limit problems related to unspecific targeting and toxicity.

Example 8

Anti-Cyclin-B1 siRNA/CADY Inhibits Proliferation of Cancer Cells

The potency of CADY/siRNA complex to block cancer cell proliferation was then investigated.

As shown on FIG. 8, the anti-cyclin B1 siRNA significantly blocks cancer cell proliferation when associated to CADY. 40% and 72% of inhibition were obtained with siRNA concentrations of 0.1 nM and 1 nM, respectively, associated to CADY-1, whereas the same concentrations were not efficient when lipofectamine was used as vector. These results are in perfect agreement with those obtained on other cell lines and confirm the high potency of CADY and the possibility of using very low concentration (sub nanomolar) of siRNA.

These data are the first demonstration that siRNA can work at concentrations lower that 1 nM. Such low concentrations of siRNA induced a strong biological response, suggesting that CADY-mediated delivery is highly efficient. This is certainly correlated with the rapid release of the siRNA in the cytoplasm, independently of the endosomal pathway.

Example 9

Anti-Cyclin-B1 siRNA/CADY Inhibits Tumor Growth: Intratumoral Injection

The effect of the anti-cyclin B1 siRNA/CADY complexes was then investigated on a tumor animal model, to determine to what extend the results obtained on the proliferation of cancer cells could be extrapolated to the inhibition of tumor growth in vivo.

The results are shown on FIG. 9. In a control experiment, the inventors observed that 20 days after injection of PBS, CADY or naked siRNA, the tumor size increased by 2,5 fold. In contrast, no growth of the tumor was observed, when injected with CADY/siRNA even with low concentration of siRNA (1 µg).

These results suggested that siRNA specifically inhibits tumor growth and, thanks to the used of CADY as carrier, only a low concentration of siRNA is required for a marked anti-tumoral effect. Moreover, a significant reduction in the tumor size was observed after a second injection of CADY/siRNA. Western blot analysis showed that the level of cyclin B1 was dramatically reduced.

These results demonstrate that CADY constitutes an excellent tool for in vivo delivery of siRNA.

Example 10

Cholesterol Modified-CADY-Formulation for In Vivo Administration

The above results demonstrate that CADY-1 constitutes an excellent tool for in vivo application of siRNA. However, although CADY-1/siRNA formulation is highly efficient upon intra-tumoral injection, the observed response to siRNA was very limited when the complexes were injected intravenously or via the intra-peritoneal route.

A new variant of CADY was hence designed to obtain nano-particles including siRNA, which are stable in vivo and administrable through intravenous injections. In that purpose, a cholesterol group was added at the N-terminus (CADY-S) or at the C-terminus (CADY-S2) of CADY. Cholesterol linking at the C-terminus was performed through a disulfide bond with the cysteamide group. Linking at the N-terminus was performed through the activation of the amino group and formation of a disulfide bond.

The ability of both CADY-S and CADY-S2 to deliver siRNA was evaluated using anti-cyclin B1 siRNA. In order to identify the optimal formulation, different molar ratios of CADY were used in complex with 50 nM siRNA. Formulations were ranked based on the G2 arrest associated to knock down of cyclin B1.

The results, presented in FIG. 10, show that the presence of cholesterol attached to CADY does not affect its efficiency to deliver siRNA in cultured cells. The optimal formulation is similar to that obtained with CADY. The optimal size for the particle is of about 200 nm diameter.

The in vivo efficiency of CADY-S was then investigated, in order to determine if the cholesterol-modified form of CADY can improve siRNA delivery through intravenous injection and block tumor growth in vivo. Experiments were performed on two tumor mouse models, in which 5PC3 or Human H1299 adenocarcinoma cells were injected subcutaneously into the flanks of NCR nude mice.

The results of both experiments demonstrate that cholesterol-modified CADY was able to deliver siRNA in vivo, and induced a significant biological response by blocking tumor growth (FIG. 11). The presence of cholesterol improves the stability of the particle after intravenous injection. Moreover, only one injection at low concentration of siRNA (10 µg) of siRNA was required to fully abolish the tumor growth.

These results constitute the first in vivo therapeutic application of a carrier system/siRNA complex using physiological doses. CADY hence appears as the best vector for systematic in vivo delivery of siRNA, since other potent methods (such as cationic polymer/cholesterol-modified siRNA) required an everyday IV injection of siRNA, at concentrations 10 fold higher than those used in the above-described experiments, to obtain a similar efficiency.

Example 11

CADY-Mediated Delivery of Therapeutic Peptides

Protein transduction technology described so far requires the attachment of the Protein Transduction Domain (PTD) to the target peptide or protein, which can be achieved either by chemical cross-linking or by cloning and expression of a fusion protein. Conjugate method offers several advantages for rationalization and control of the stoechiometry, as well as for reproducibility and calibration of the PTD-cargo for in vivo application. However, this approach is limited from a technical point of view and by a risk of alteration of the biological activity of the cargoes.

CADY vectors, especially CADY-2 vectors, offer an alternative to the covalent PTDs technology, for the delivery of full-length proteins and peptides into mammalian cells.

In higher eukaryotes, the cell cycle progression is coordinated by several closely related Ser/Thr protein kinases, resulting from association of a catalytic Cyclin-dependent kinase (CDK) subunit with a regulatory cyclin subunit. CDK/cyclin complexes are regulated by both phosphorylation/dephosphorylation and protein-protein interactions with different partners, including structural CDK inhibitors (CKI). Genetic evidence supports a strong correlation between alterations in the regulation of CDKs and the molecular pathology of cancer. Thus, in the past few years, there has been considerable interest in the development of inhibitors of CDK protein kinases. A greater understanding of the cell cycle and of the inherent complexity of CDK regulation now offers a number of possible routes to their inhibition (Swanton 2004). One of the currently most developed strategies to inhibit CDKs is based on the design of small molecules that target the ATP-binding site, thereby interfering directly with their catalytic activity.

The tumor suppressor protein p27 is essential in the control of the G1/S transition. Alteration in p27 regulation results in aberrations in cell cycle progression and development of tumors. p27 protein interacts with the Cdk/cyclin complex in order to maintain the complex in an inactive conformation which controls the rate of the G1 phase. The molecular mechanism by which p27 induces cell cycle arrest was investigated in details, and peptide motifs which block both cell cycle in G1 and cancer cell proliferation have been identified.

Based on the X-ray structure of the cdk2/cyclinA/p27 complex (Jeffrey, Russo et al. 1995), the inventors have selected three peptides:

p1p27: RVSNGSPSLERMDARQAEHPKPSACRNL (SEQ ID No: 22)
pRXL: PSLERMDAR (SEQ ID No: 23), and
p2p27: NRTEENVSDGSPNAGSVEQTPKKPGLR (SEQ ID No: 24) as a negative control.

Peptides were synthesized and purified as described previously (Mery, Granier et al. 1993; Morris, Vidal et al. 1997), then their ability to alter the cell cycle progression was investigated.

As shown on FIG. 12, the delivery of the peptides p1p27 or pRXL induced a cell cycle arrest in G1 in all tested cell lines. In contrast, no effect was observed with CADY or free p1p27, which suggested that CADY dramatically improves the cellular uptake of the peptide, without any toxicity associated to the carrier. Moreover, the fact that no effect was observed with the control peptide p2p27 demonstrates the high specificity of the peptide. In comparison to results previously published with pRXL using a TAT or Pen covalent based strategy (Nagahara, Vocero-Akbani et al. 1998; Chen, Sharma et al. 1999; Snyder, Meade et al. 2003), the efficiency with CADY strategy is at least 2-fold better.

Example 12

CADY2-Mediated In Vivo Delivery of p27 Inhibits Tumor Growth

The inventors then investigated the ability of the p1p27/CADY complexes to block tumor growth in vivo.
The results are shown on FIG. 13.

In control experiments, in which PBS, CADY alone or naked p1p27 were injected, the tumor size had increased by 5-fold, 5 weeks after injection. In contrast, no growth of the tumor was observed, when injected with CADY/p1p27. These results suggest that p1p27 specifically inhibits tumor growth, and that the use of CADY as carrier enables to administer only a low amount of p1p27 for a marked anti-tumoral effect. Moreover, a significant reduction in the tumor size was observed after a second injection of CADY/p1p27. These results show that CADY constitutes an excellent tool for in vivo application of therapeutic peptides.

Other experiments, performed with peptides having an anti-viral or an antitumoral activity, as described in (Morris, Robert-Hebmann et al. 1999) or in (Gondeau, Gerbal-Chaloin et al. 2005), demonstrated that CADY-2 peptides improve the delivery of several distinct proteins and peptides into different cell lines in a fully biologically active form, without the need for prior chemical covalent coupling or denaturation step. CADY technology hence constitutes a powerful tool for basic research, and demonstrated to be extremely powerful for studying the role of proteins, and for targeting specific protein/protein interactions in vitro as well as in vivo.

REFERENCES

Allen, T. M. (2002). "Ligand-targeted therapeutics in anticancer therapy." Nat Rev Cancer 2(10): 750-63.
Chen, Y. N., S. K. Sharma, et al. (1999). "Selective killing of transformed cells by cyclin/cyclin-dependent kinase 2 antagonists." Proc Natl Acad Sci USA 96(8): 4325-9.
Deshayes, S., M. C. Morris, et al. (2005). "Cell-penetrating peptides: tools for intracellular delivery of therapeutics." Cell Mol Life Sci 62(16): 1839-49.
El-Andaloussi, S., T. Holm, et al. (2005). "Cell-penetrating peptides: mechanisms and applications." Curr Pharm Des 11(28): 3597-611.
Elliott, G. and P. O'Hare (1997). "Intercellular trafficking and protein delivery by a herpesvirus structural protein." Cell 88(2): 223-33.
Gondeau, C., S. Gerbal-Chaloin, et al. (2005). "Design of a novel class of peptide inhibitors of cyclin-dependent kinase/cyclin activation." J Biol Chem 280(14): 13793-800.
Gratton, J. P., J. Yu, et al. (2003). "Cell-permeable peptides improve cellular uptake and therapeutic gene delivery of replication-deficient viruses in cells and in vivo." Nat Med 9(3): 357-62.
Jarver, P. and U. Langel (2004). "The use of cell-penetrating peptides as a tool for gene regulation." Drug Discov Today 9(9): 395-402.
Jeffrey, P. D., A. A. Russo, et al. (1995). "Mechanism of CDK activation revealed by the structure of a cyclinA-CDK2 complex." Nature 376(6538): 313-20.
Joliot, A. and A. Prochiantz (2004). "Transduction peptides: from technology to physiology." Nat Cell Biol 6(3): 189-96.
Mery, J., C. Granier, et al. (1993). "Disulfide linkage to polyacrylic resin for automated Fmoc peptide synthesis. Immunochemical applications of peptide resins and mercaptoamide peptides." Int J Pept Protein Res 42(1): 44-52.
Morris, M. C., L. Chaloin, et al. (2000). "Translocating peptides and proteins and their use for gene delivery." Curr Opin Biotechnol 11(5): 461-6.

Morris, M. C., L. Chaloin, et al. (2002). "Signal sequence based Cell Penetratine Peptides and theirs applications for gene delivery." *Cell Penetrating peptides: Processes and application*.

Morris, M. C., V. Robert-Hebmann, et al. (1999). "A new potent HIV-1 reverse transcriptase inhibitor. A synthetic peptide derived from the interface subunit domains." *J Biol Chem* 274(35): 24941-6.

Morris, M. C., P. Vidal, et al. (1997). "A new peptide vector for efficient delivery of oligonucleotides into mammalian cells." *Nucleic Acids Res* 25(14): 2730-6.

Nagahara, H., A. M. Vocero-Akbani, et al. (1998). "Transduction of full-length TAT fusion proteins into mammalian cells: TAT-p27Kip1 induces cell migration." *Nat Med* 4(12): 1449-52.

Pooga, M., M. Hallbrink, et al. (1998). "Cell penetration by transportan." *Faseb J* 12(1): 67-77.

Schwarze, S. R., A. Ho, et al. (1999). "In vivo protein transduction: delivery of a biologically active protein into the mouse." *Science* 285(5433): 1569-72.

Snyder, E. L., B. R. Meade, et al. (2003). "Anti-cancer protein transduction strategies: reconstitution of p27 tumor suppressor function." *J Control Release* 91(1-2): 45-51.

Swanton, C. (2004). "Cell-cycle targeted therapies." *Lancet Oncol* 5(1): 27-36.

Wadia, J. S. and S. F. Dowdy (2002). "Protein transduction technology." *Curr Opin Biotechnol* 13(1): 52-6.

Wadia, J. S., R. V. Stan, et al. (2004). "Transducible TAT-HA fusogenic peptide enhances escape of TAT-fusion proteins after lipid raft macropinocytosis." *Nat Med* 10(3): 310-5.

The invention claimed is:

1. A cell-penetrating peptide comprising an amino acid sequence selected from the group consisting of

| | |
|---|---|
| GLWRALWRLLRSLWRLLWKA; | (SEQ ID No: 2) |
| GLWRALWRALWRSLWKLKRKV; | (SEQ ID No: 3) |
| GLWRALWRALRSLWKLKRKV; | (SEQ ID No: 4) |
| GLWRALWRGLRSLWKLKRKV; | (SEQ ID No: 5) |
| GLWRALWRGLRSLWKKKRKV; | (SEQ ID No: 6) |
| GLWRALWRLLRSLWRLLWKA; | (SEQ ID No: 7) |
| GLWRALWRALWRSLWKLKWKV; | (SEQ ID No: 8) |
| GLWRALWRALWRSLWKSKRKV; | (SEQ ID No: 9) |
| GLWRALWRALWRSLWKKKRKV; and | (SEQ ID No: 10) |
| GLWRALWRLLRSLWRLLWSQ. | (SEQ ID No: 11) | and wherein the cell penetrating peptide comprises, covalently linked to the N-terminal end of said amino acid sequence, one or more chemical entities selected from the group consisting of an acetyl, a fatty acid, a cholesterol, a poly-ethylene glycol, a nuclear localization signal, and a targeting molecule.

2. A cell-penetrating peptide, which is CADY-1 (Ac-GL-WRALWRLLRSLWRLLWKA-Cya)(SEQ ID NO:2) or CADY-2 (Ac-GLWRALWRALWRSLWKLKWKV-Cya) (SE ID NO:8).

3. A complex comprising a cell-penetrating peptide and a cargo selected from the group consisting of nucleic acids, peptides, proteins, contrast agents, and toxins, wherein the amino acid sequence of the cell-penetrating peptide is selected from

| | |
|---|---|
| GLWRALWRLLRSLWRLLWKA; | (SEQ ID No: 2) |
| GLWRALWRALWRSLWKLKRKV; | (SEQ ID No: 3) |
| GLWRALWRALRSLWKLKRKV; | (SEQ ID No: 4) |
| GLWRALWRGLRSLWKLKRKV; | (SEQ ID No: 5) |
| GLWRALWRGLRSLWKKKRKV; and | (SEQ ID No: 6) |
| GLWRALWRGLRSLWKKKRKV. | (SEQ ID No: 7) |

4. The complex of claim 3, wherein said cargo is a siRNA selected to silence a target mRNA.

5. A complex comprising a cell penetrating peptide and a cargo, wherein said cargo is a peptide or a protein, and wherein the amino acid sequence of the cell penetrating peptide is selected from the group

```
GLWRALWRALWRSLWKLKWKV        (SEQ ID No: 8)
GLWRALWRALWRSLWKSKRKV        (SEQ ID No: 9)
GLWRALWRALWRSLWKKKRKV        (SEQ ID No: 10)
GLWRALWRALWRSLWKLKRKV        (SEQ ID No: 3)
GLWRALWRLLRSLWRLLWSQ         (SEQ ID No: 11)
GLWRALWRLLRSLWRLLWSQPKKKRKV. (SEQ ID No: 12)
```

* * * * *